United States Patent [19]

Wagner et al.

[11] Patent Number: 4,551,302

[45] Date of Patent: Nov. 5, 1985

[54] DENTAL ALLOY BASED ON PALLADIUM FOR THE PRODUCTION OF FIXED AND REMOVABLE DENTAL CONSTRUCTIONS

[75] Inventors: Rudolph Wagner, Remchingen; Harry Schiwiora, Pforzheim, both of Fed. Rep. of Germany

[73] Assignee: Degussa Aktiengesellschaft, Frankfurt, Fed. Rep. of Germany

[21] Appl. No.: 607,701

[22] Filed: May 7, 1984

[30] Foreign Application Priority Data

May 6, 1983 [DE] Fed. Rep. of Germany ....... 3316595

[51] Int. Cl.$^4$ .............................................. C22C 5/04
[52] U.S. Cl. .................................. 420/464; 420/465; 433/207
[58] Field of Search ................ 420/463, 464, 465; 433/200, 207

[56] References Cited

U.S. PATENT DOCUMENTS

| 2,310,732 | 2/1943 | Dietz | 420/465 |
| 4,179,288 | 12/1979 | Prosen | 420/463 |
| 4,319,877 | 3/1982 | Boyajian | 420/463 |
| 4,336,290 | 6/1982 | Tsai | 420/463 |
| 4,387,072 | 6/1983 | Schaffer | 420/464 |
| 4,400,350 | 8/1983 | Wagner | 420/464 |
| 4,419,325 | 12/1983 | Prasad | 420/464 |

FOREIGN PATENT DOCUMENTS 2440425 6/1976 Fed. Rep. of Germany .

*Primary Examiner*—L. Dewayne Rutledge
*Assistant Examiner*—Robert L. McDowell
*Attorney, Agent, or Firm*—Cushman, Darby & Cushman

[57] ABSTRACT

Cast alloys which should be suited for both the production of removable dental construction (model casting technique) and also for permanent crowns and bridges with ceramic facing (firing technique) must combine good firing properties and good tensile strength and strain values. Alloys of this type consist of 65–85% Pd, 0–10% Au and/or 0–5% Pt, 0.1–10% Sn, 1–10% Ga, 1–12% Cu as well as 0.5–1.5 Ru and/or 0.05–0.7% Re.

3 Claims, No Drawings

DENTAL ALLOY BASED ON PALLADIUM FOR THE PRODUCTION OF FIXED AND REMOVABLE DENTAL CONSTRUCTIONS

BACKGROUND OF THE INVENTION

This invention is directed to a dental alloy based on palladium for the production of fixed and removeable dental constructions. As a result it can be used in the same manner for firing on dental porcelain as well as model casting alloy and for combined dental constructions.

It is known to employ together in the mouth prosthesis elements made of base Co-Cr alloys on the one hand and on the other hand fired dental constructions made of high gold content alloys having a ceramic facing. The permanent contact of materials with different corrosion potentials, however, can form quite stable corrosion elements in the mouth.

Therefore there is the desire to employ only a single material in the oral cavity. Previous attempts for ceramic facing of Co-Cr as alloys have been ruined because firing properties for dental porcelain were not satisfactory; with high gold content alloys, the high specific weight, the lower modulus of elasticity and also the high price of gold make them appear to be unsuited for use as an alloy for the model casting technique.

Because of their resistance to corrosion, specific gravity, material costs and mechanical properties palladium alloys would be suitable materials with which there can be executed both prosthesis parts as well as porcelain fused to metal operations.

In order to guarantee the mechanical stability in the mouth and also a resistance to deformation upon taking out a prosthesis the alloys used for those purposes should have a 0.2%-yield strength of at least 550 Mpa and an elongation at break of at least 4% according to DIN 13912 (German Industrial Standard 13912).

Previously known porcelain fused to metal alloys based on palladium (e.g. German AG 2440425, Tsai U.S. Pat. No. 4,336,290, Boyajian U.S. Pat. No. 4,319,877 or Prosen U.S. Pat. No. 4,179,288) fulfill the requirement in regard to the 0.2% yield strength ($R_p$ 0.2), however, the elongation is at maximum 2-3%. This is chiefly related to the dendritic structure which only permits minimal deformations.

It is above all decisive for the usability of an alloy for veneering with dental ceramic compositions that the coefficient of thermal expansion (WAK) of the alloy be suited to that of the ceramic composition in the range from room temperature to 600° C., namely so that it is always somewhat larger in this temperature range.

Therefore, it was the problem of the invention to find dental alloys based on palladium which can be used for the production of both fixed as well as removable dental constructions and therefore have to have a sufficiently high 0.2% yield strength and also a sufficient high elongation and can be veneered with dental ceramics.

SUMMARY OF THE INVENTION

This problem has been solved according to the invention by making alloys consisting of (or consisting essentially of) 65-85% palladium, 0-10% gold and/or 0-5% platinum, 0.1-10% tin, 1-10% gallium, 1-12% copper, as well as 0.05-1.5% ruthenium and/or 0.05-0.7%, e.g. 0.2-0.7%, rhenium. The percentages are by weight.

Preferably there are used alloys which contain 65 to 80%, especially 78-80% palladium, 0.5 to 5%, especially 0.8 to 2% gold, 0.5 to 5%, especially 0.8 to 2% platinum, 3 to 8%, especially 3 to 5% copper, 4 to 8%, especially 5 to 6% gallium, 4 to 9%, especially 6 to 9% tin, and 0.2 to 0.9%, especially 0.4 to 0.6% rhenium or 0.7 to 0.9% ruthenium.

The strength of those alloys is controlled essentially by the addition of gallium and the fine grain quality needed for good elongation properties is attained through the addition of platinum and ruthenium or rhenium. The necessary coefficient of thermal expansion is adjusted through a combination of the additional elements gold, copper, gallium and tin.

Especially proved alloys are made of (in wt.%)

(1) 80% Pd, 1% Au, 1% Pt, 5% Cu, 6% Ga, 6.5 Sn, 0.5 Re
(2) 80% Pd, 1.5% Au, 1.5% Pt, 3% Cu, 5% Ga, 8.5 Sn, 0.5% Re
(3) 80% Pd, 1% Pt, 5% Cu, 6% Ga, 6.5% Sn, 0.5% Ru
(4) 79.7% Pd, 1% Au, 1% Pt, 5% Cu, 6% Ga, 6.5% Sn, 0.8% Ru
(5) 81.2% Pd, 5% Cu, 6% Ga, 7% Sn, 0.8% Ru
(6) 70% Pd, 5% Au, 5% Pt, 4% Sn, 9% Cu, 6.3% Ga, 0.5% Ru, 0.2 Re

Melting range hardness, 0.2% yield strength elongation at break and grain size of these six alloys are set forth in the following table.

The alloys of the invention possess very good flow properties and in the temperature range 20°-600° C. have a coefficient of expansion between 13.5 and $14.5 \times 10^{-6}$/° C.; their mechanical properties are only neglibly changeable by heat treatment. The alloys can be cold worked very well.

The presence of tin is very important in the alloys of the invention since this like gallium reduces the melting point. In contrast to gallium, however, it causes no substantial increase in hardness."

TABLE

| Alloy | Melting Range (°C.) | Vickers Hardness (HV5/30) | Yield Strength 0.2% (MPa) | Elongation at Break (%) | Number of grains (grains/mm$^2$) |
|---|---|---|---|---|---|
| 1 | 1290–1160 | 271 | 585 | 36.6 | About 6000 |
| 2 | 1320–1160 | 249 | 559 | 36.5 | About 6000 |
| 3 | 1280–1175 | 257 | 597 | 13.8 | About 2300 |
| 4 | 1290–1155 | 260 | 638 | 15.8 | About 3000 |
| 5 | 1290–1155 | 270 | 599 | 6.0 | About 4000 |
| 6 | 1255–1080 | 290 | 737 | 17.3 | About 3500 |

*Measured on test bodies according to DIN 13912

What is claimed is:

1. A dental alloy suitable for the production of fixed and removal dental constructions consisting essentially of 65–80% palladium, 0.5–5% gold, 0.5–5% platinum, 3–8% copper, 4–8% gallium, 4–9% tin and 0.2–0.7% rhenium or 0.7–0.9% ruthenium.

2. A dental alloy according to claim 1 consisting essentially of 78–80% palladium, 0.8–2% gold, 0.8–2% platinum, 3–5% copper, 5–6% gallium, 6–9% tin and 0.4–0.6% rhenium or 0.7 to 0.9% ruthenium.

3. A dental alloy according to claim 2 consisting of 80% palladium, 1% gold, 1% platinum, 5% copper, 6% gallium, 6.5% tin and 0.5% rhenium.

* * * * *